(12) United States Patent
Rosenblood et al.

(10) Patent No.: US 6,428,554 B1
(45) Date of Patent: Aug. 6, 2002

(54) DUAL ACTION TONGUE SCRAPER

(75) Inventors: Kenneth L. Rosenblood, Los Angeles; Robert G. Hayman, Pacific Palisades, both of CA (US)

(73) Assignee: Discus Dental Impressions, Inc., Culver City, CA (US)

( * ) Notice: Subject to any disclaimer, the term of this patent is extended or adjusted under 35 U.S.C. 154(b) by 0 days.

(21) Appl. No.: 09/629,297

(22) Filed: Jul. 31, 2000

Related U.S. Application Data

(60) Division of application No. 09/223,898, filed on Dec. 31, 1998, which is a continuation-in-part of application No. 08/917,245, filed on Aug. 25, 1997, now Pat. No. 5,868,769.

(51) Int. Cl.[7] ............................................... A61B 17/24
(52) U.S. Cl. ..................................................... 606/161
(58) Field of Search .............................. 606/162, 161, 606/160, 1; 15/111, 110, 160, 167.1

(56) References Cited

U.S. PATENT DOCUMENTS

| | | | |
|---|---|---|---|
| 1,893,524 A | * 1/1933 | Shanley | 606/161 |
| 3,477,435 A | 11/1969 | Artelli | 128/304 |
| 3,890,964 A | 6/1975 | Castanedo | 128/62 |
| 4,455,704 A | 6/1984 | Williams | 15/111 |
| 5,005,246 A | * 4/1991 | Yen-Hui | 606/161 |
| 5,217,475 A | * 6/1993 | Kuber | 606/161 |
| D361,618 S | * 8/1995 | Patel | D24/133 |
| 5,569,278 A | * 10/1996 | Persad | 606/161 |

FOREIGN PATENT DOCUMENTS

FR     2568465     8/1984 .................. 606/161

\* cited by examiner

Primary Examiner—Henry J. Recla
Assistant Examiner—Vy Q. Bui
(74) Attorney, Agent, or Firm—Christie, Parker & Hale, LLP

(57) ABSTRACT

A dual action tongue scraper provides either a hard scrape or a soft scrape of the tongue, as desired. A hard scraping surface and a soft scraping surface are formed along at least one of the edges of a strip of flexible material. A user bends the strip of flexible material such that generally only one of the hard scraping surface and the soft scraping surface contacts the user's tongue at a given time during scraping.

19 Claims, 4 Drawing Sheets

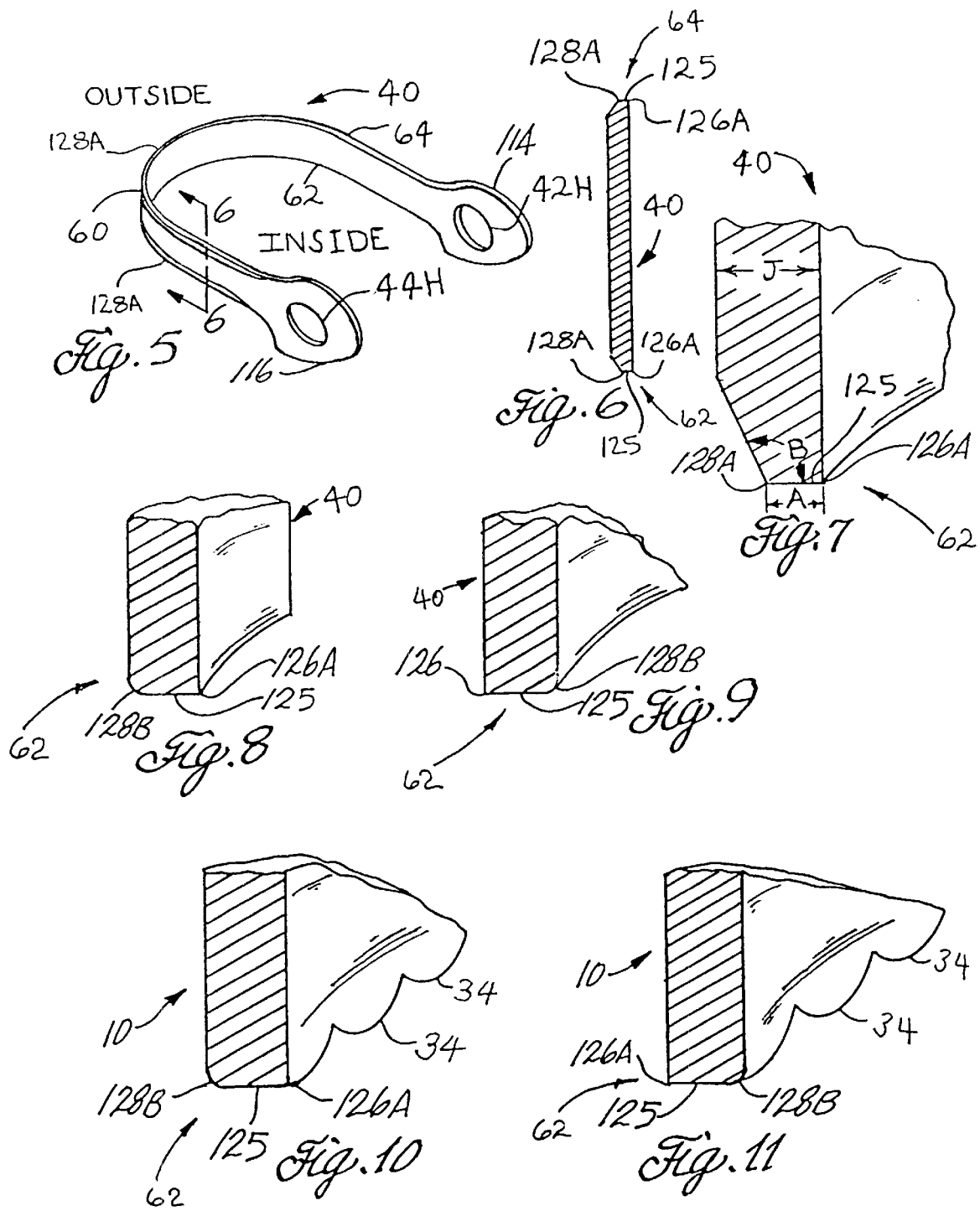

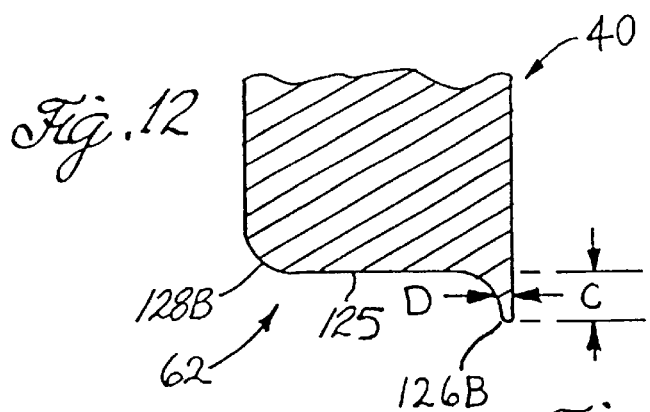
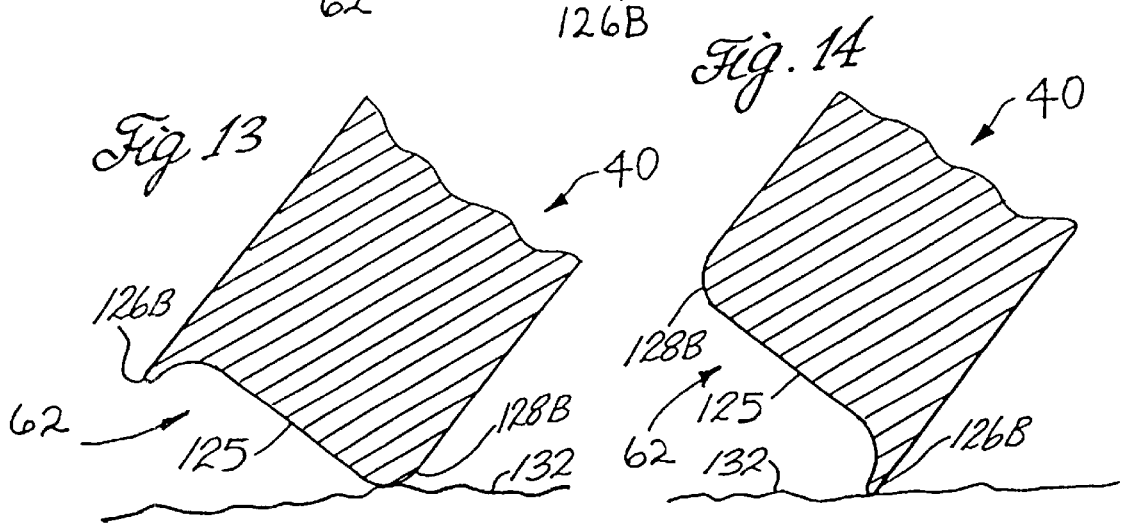
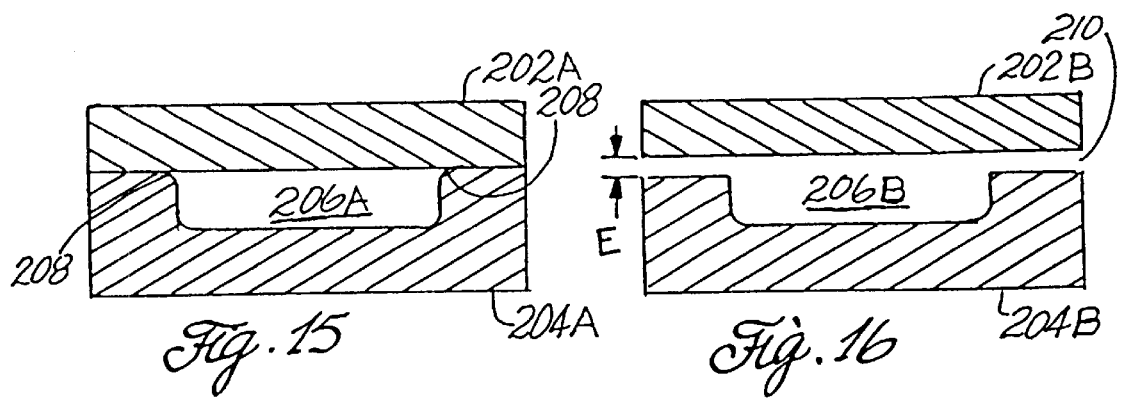

DUAL ACTION TONGUE SCRAPER

CROSS REFERENCE TO RELATED APPLICATIONS

This application is a divisional of pending application Ser. No. 09/223,898, filed Dec. 31, 1998, which is a continuation-in-part of application No. 08/917,245, filed Aug. 25, 1997, which issued as U.S. Pat. No. 5,868,769), the disclosures of both are incorporated fully herein by reference.

FIELD OF INVENTION

The present invention relates generally to devices for promoting dental hygiene, and relates more particularly to a dual action tongue scraper for cleansing food debris, volatile sulfur compounds, dead cells, microflora and other microorganisms from the tongue. The dual action tongue scraper is configured to provide either a hard scrape or a soft scrape, as desired.

BACKGROUND OF INVENTION

The human tongue is slightly furry in texture and has numerous protuberances, e.g., papillae, which convey to the brain the senses of taste and touch. Consequently, the tongue can easily become a breeding ground for microorganisms such as bacteria, as well as a repository for food debris, volatile sulfur compounds (which are a major cause of halitosis) and dead cells. Over time, some of the collected material becomes a soft plaque which is another cause of bad breath. This soft plaque is known to attack the teeth and gums. Tests have shown that daily scraping to reduce the amount of coating on the tongue eliminates much of the undesirable bacteria and sulfur compounds, thus significantly inhibiting plaque formation on the teeth in the long term, and substantially reducing halitosis in the short term.

A wide variety of tongue scrapers are known in the dental hygiene arts. For example, U.S. Pat. No. 3,477,435 to Artelli discloses a tongue scraper with a metal blade-like member having an end portion formed to fit between wooden handle parts. A rigid blade-like portion extends forwardly of the handle at the other end in a curve which is configured either for a right-handed person or for a left-handed person.

U.S. Pat. No. 3,890,964 to Castanedo discloses a one-piece tongue scraper which includes an elongated handle at one end with longitudinally diverging arms at the other end. The ends of the arms are connected by a longitudinally bowed cross bar having a laterally centered, arched portion and beveled edge faces.

U.S. Pat. No. 4,455,704 to Williams discloses a tongue cleaner in combination with a toothbrush. The tongue cleaner is an arcuate scraper member which is centrally secured to the tooth brush handle at the end opposite the brush.

U.S. Pat. No. 5,217,475 to Kuber discloses a disposable tongue scraper which is intended to be used only once. The normally planar scraper is formed of a flexible, resilient material and includes opposed outer portions having smooth generally parallel edges. Each outer portion terminates in a rounded free end portion. An elongated central portion having a serrated edge is disposed between the two outer portions. Holding one end portion firmly in each hand and bending the scraper into a U-shape, the user contacts the extended tongue with the serrated edge and then scrapes gently from back to front to remove accumulated coating material.

It is believed that many users would prefer a choice of different scraping capabilities. Some users may prefer a more effective scrape, even though the more effective scrape is harsher. Other users may prefer a less harsh, though less effective, scrape. Thus, it is desirable to provide a tongue scraper which allows users to easily choose the type, i.e., hard or soft, of scrape to be performed therewith.

SUMMARY OF THE INVENTION

In a first aspect of the invention there is provided a dual action tongue scraper comprised of a strip of flexible material including two opposed generally planar end portions, and a generally planar central portion disposed between the two end portions. The strip of flexible material also includes two edges thereof. Each edge of the strip of flexible material extends along the generally planar central portion between the two end portions.

The dual action tongue scraper is configured to provide a comparatively hard scrape when the tongue scraper is bent one way, such that the tongue contacts a hard scraping surface which extends along one edge thereof; and is configured to provide a comparatively soft scrape when the tongue scraper is bent another way, such that the tongue contacts a soft scraping surface which extends along either the same or a different edge thereof. The hard scrape is generally more effective at removing the undesirable coating from the tongue, but the hard scrape may be too harsh for some people.

When formed upon a common edge, the hard scraping surface and the soft scraping surface are separated by a generally flat portion of the common edge, so as to facilitate scraping of the tongue with only the desired one of the hard scraping surface and the soft scraping surface.

In cross section, the hard scraping surface preferably comprises an orthogonal corner (having an angle of approximately 90 degrees) and the soft scraping surface preferably comprises an obtuse corner (having an angle which is substantially greater than 90 degrees). More particularly, the soft scraping surface preferably comprises an obtuse corner having an angle of approximately 108 degrees.

Alternatively, the soft scraping surface comprises a substantially round corner. The round corner preferably has a radius of between approximately 0.005 inch and approximately 0.030 inch, preferably approximately 0.010 inch.

One or both of the two edges may comprise a hard scraping surface and/or a soft scraping surface, as desired.

Each of the two edges may either be configured as a smooth edge or a serrated edge, as desired. Further, each of the two edges may comprise either a substantially straight edge or a convex edge, as desired.

As used herein, the term "serration" is defined to include any crenellation, tooth, appendage, protuberance or any other projection, whether regular or irregular, a plurality of which extend in a generally spaced apart fashion from an edge of the tongue scraper to enhance scraping of the tongue.

According to an alternative aspect of the present invention, the hard scraping surface comprises a protrusion extending from at least one edge of the strip of flexible material. The protrusion preferably has a length of between approximately 0.004 inch and approximately 0.012 inch, preferably approximately 0.008 inch, and preferably has an average thickness of between approximately 0.0005 inch and approximately 0.005 inch, preferably approximately 0.001 inch.

Such protrusions are preferably formed during injection molding of the tongue scraper. The protrusions may be formed either by defining the protrusions as part of the mold cavity, or alternatively, by causing the protrusions to be defined by controlled flashing. Controlled flashing may be formed by machining the mating mold sections to a desired degree of flatness, such as 0.001 inch for example, and then injecting polymer into the mold cavity at a pressure which results in the desired degree of flashing, such as 15,000 psi for example. Those skilled in the art will appreciate that various other combinations of mold mating surface flatness and injection molding pressure are likewise suitable for providing a desired amount of flashing. Generally, providing flatter mating surfaces of the mold sections will require a higher injection pressure and providing less flat surfaces of the mold sections will require a lower injection pressure, in order to form a given controlled amount of flashing.

As those skilled in the art will appreciate, various other methods, e.g., machining, etching, grinding, etc., are likewise suitable for forming a protrusion upon a desired edge of the tongue scraper.

The hard scraping surface, whether an orthogonal corner or a protrusion, and the soft scraping surface, whether an obtuse corner or a round corner, each extend generally along the length of the central portion of the tongue scraper, and thus extend generally from one end portion to the other end portion.

According to the present invention, a person's tongue is scraped by grasping the flexible strip with one hand at each of two ends of the flexible strip and bending the flexible strip into a generally U-shaped configuration such that either the hard scraping surface or the soft scraping surface is along the inside portion of the U-shaped flexible strip. The tongue is then scraped with the inside portion of the U-shaped flexible strip.

Thus, by bending the flexible strip so as to position the hard scraping surface along the inside of the U-shaped flexible strip, a hard scrape is provided. Conversely, by bending the flexible strip so as to position the soft scraping surface along the inside of the U-shaped flexible strip, a soft scrape is provided. In this manner, the person may easily obtain either a hard scrape or a soft scrape, as desired.

Alternatively, scraping may be performed without bending the flexible strip. If desired, the flexible strip may be held at each end thereof, such that the flexible strip remains substantially straight. The desire one of the hard scraping surface and the soft scraping surface is then used to effect scraping.

As mentioned above, the central portion is optionally bounded longitudinally by a convexly arcuate edge and a generally linear edge. A multiplicity of optional serrations on the convex edge may be used to scrape planar areas of the tongue upper surface. The convex and linear edges may alternatively both have a smooth surface. In one configuration of the invention, a hole in each end portion allows the user to firmly grip the end portions between thumb and finger.

In another aspect, the invention provides a tongue scraper fabricated from a resilient material and including opposed generally planar end portions each end portion preferably terminating in a generally elliptical arcuate edge and extending proximally in a neck having arcuate edges tapering to a predetermined width. The edges each have a plurality of serrations. The tongue scraper further includes a generally planar central portion disposed symmetrically between and contiguous to the tapered neck of each end portion. The central portion is determined longitudinally by a convexly arcuate edge having a multiplicity of serrations, and a generally linear edge similarly having a multiplicity of serrations.

In yet another aspect, the invention provides a tongue scraper fabricated from a resilient material and including opposed generally planar end portions each terminating in a generally elliptical arcuate edge and extending proximally in a neck having arcuate edges tapering to a predetermined width. The edges each have a smooth surface. The tongue scraper further includes a generally planar central portion disposed symmetrically between and contiguous to the tapered neck of each end portion. The central portion is determined longitudinally by a convexly arcuate edge having a smooth surface, and a generally linear edge having a smooth surface.

BRIEF DESCRIPTION OF THE DRAWINGS

These and other features, aspects, and advantages of the present invention will be more fully understood when considered with respect to the following detailed description, appended claims and accompanying drawings, wherein:

FIG. 5 is a perspective view of the tongue scraper of FIGS. 3 and 4, bent into a generally U-shaped configuration to facilitate use thereof;

FIG. 6 is a cross-sectional side view of the tongue scraper of FIG. 5, taken along line 6 thereof and showing an orthogonal corner defining a hard scraping surface and an obtuse corner defining a soft scraping surface formed along each of the two edges thereof;

FIG. 7 is an enlarged perspective view, partially in section, showing the orthogonal corner and obtuse corner of FIG. 6, wherein the tongue scraper is bent (thereby positioning the orthogonal corner inside the U-shape) so as to provide a hard scrape therewith;

FIG. 8 is an enlarged perspective view, partially in section, showing an alternative round corner defining the soft scraping surface, wherein the tongue scraper is bent (thereby positioning the orthogonal corner inside the U-shape) so as to provide a hard scrape therewith;

FIG. 9 is a perspective view, partially in section, of the tongue scraper of FIG. 8, wherein the tongue scraper is bent (thereby positioning the round corner inside the U-shape) so as to provide a soft scrape therewith;

FIG. 10 is a perspective view, partially in section, of a tongue scraper having serrations formed along an edge thereof, as in FIGS. 1 and 2, wherein the tongue scraper is bent (thereby positioning the orthogonal corner inside the U-shape) so as to effect a hard scrape therewith;

FIG. 11 is a perspective view, partially in section, of a tongue scraper having serrations formed along an edge thereof, as in FIGS. 1 and 2, wherein the scraper is bent (thereby positioning the round corner inside the U-shape) so as to effect a soft scrape therewith;

FIG. 12 is a cross-sectional side view of a tongue scraper having a hard scraping surface and a soft scraping surface formed upon a common edge, wherein the hard scraping surface is defined by a protrusion extending from the edge;

FIG. 13 shows the tongue scraper of FIG. 12 in use, wherein the round corner defining the soft scraping surface thereof is used to effect a soft scrape;

FIG. 14 shows the tongue scraper of FIG. 12 in use, wherein the protrusion defining the hard scraping surface thereof is used to effect a hard scrape;

FIG. 15 is a cross-sectional end view of a mold used to form a tongue scraper having protrusions extending from both edges thereof, the protrusions being defined by the mold cavity; and FIG. 16 is a cross-sectional end view of a mold used to form a tongue scraper having protrusions extending from both edges thereof, the protrusions being defined by a parting line between the two mold sections.

DETAILED DESCRIPTION

Figure 1:
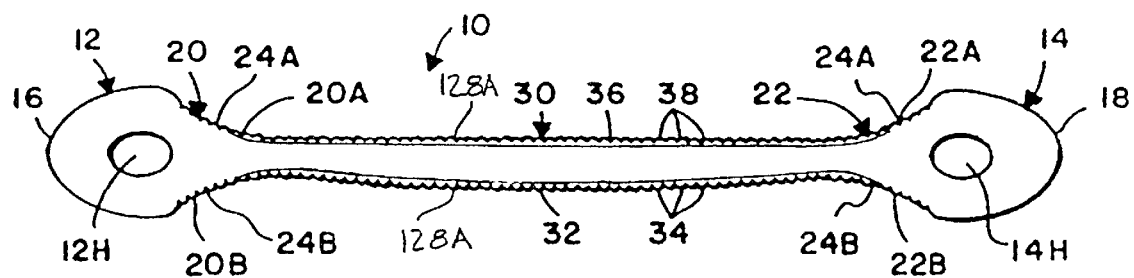
FIG. 1 is a plan view of a dual action tongue scraper according to the invention, including a central portion having a convex first edge and a linear second edge, each edge with a multiplicity of serrations formed thereon.

While the present invention is open to various modifications and alternative constructions, the preferred embodiments shown in the drawings will be described herein in detail. It is to be understood, however, there is no intention to limit the invention to the particular forms disclosed. On the contrary, it is intended that the invention cover all modifications, equivalences and alternative constructions falling within the spirit and scope of the invention as expressed in the appended claims.

Figure 2:
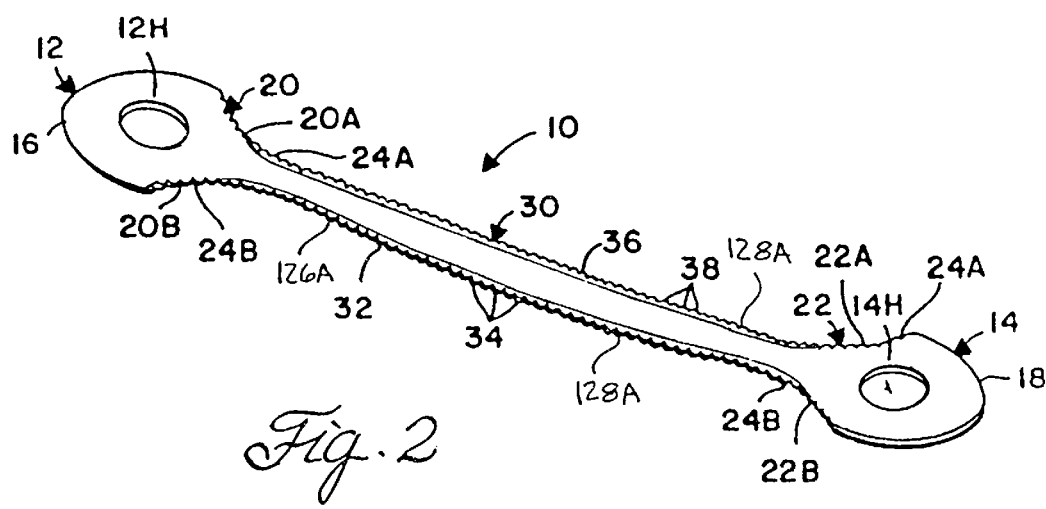
FIG. 2 is a perspective view of the FIG. 1 tongue scraper.

Referring to FIGS. 1 and 2, there is shown a serrated edge dual action tongue scraper 10 adapted for scraping coating material such as food debris, volatile sulfur compounds, dead cells and microflora from the upper surface of a tongue. The tongue scraper 10 includes opposed first and second generally planar end portions 12 and 14, respectively, each terminating distally in a generally elliptical arcuate edge 16 and 18, respectively, and each having therethrough a hole 12H and 14H, respectively. Each end portion 12 and 14 extends proximally in a neck 20 and 22, respectively, with each neck having first and second arcuate edges 20A, 20B, 22A and 22B, respectively, tapering to a predetermined width. The edges 20A, 22A, 20B and 22B have a plurality of serrations 24A and 24B, respectively. The tongue scraper 10 further includes a generally planar central portion 30 disposed symmetrically between and smoothly contiguous to the end portion necks 20 and 22. The central portion 30 is defined longitudinally by a convexly arcuate first edge 32 having a multiplicity of serrations 34 formed thereon, and a generally linear second edge 36 having a multiplicity of serrations 38 thereon.

Figure 3:
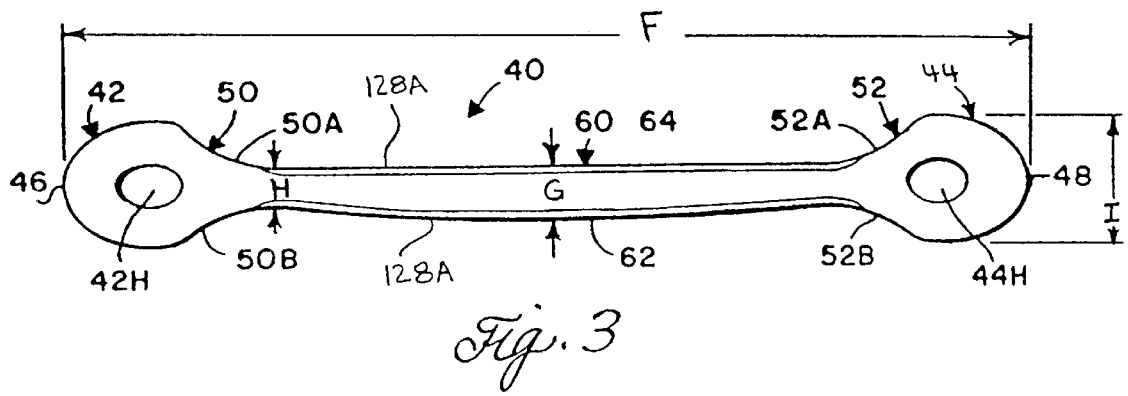
FIG. 3 is a plan view of a dual action tongue scraper according to the invention, including a central portion having smooth convex and linear edges.
Figure 4:
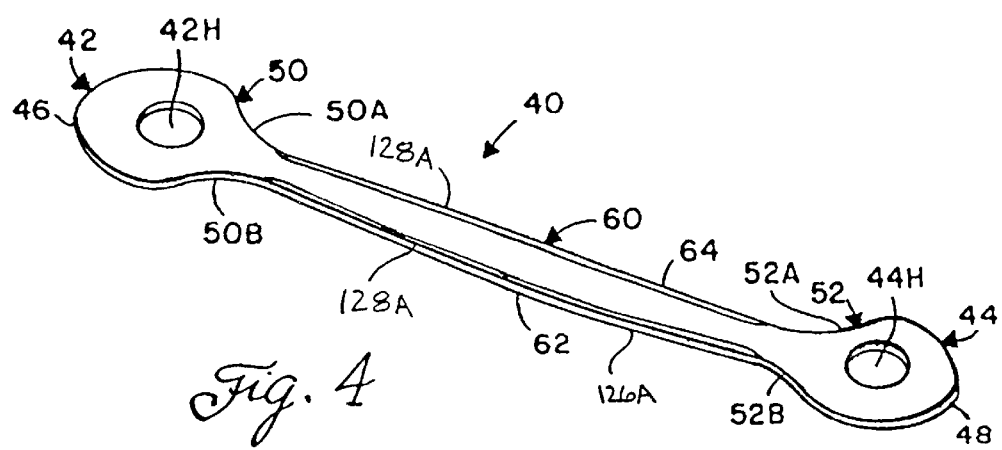
FIG. 4 is a perspective view of the FIG. 3 tongue scraper.

Referring to FIGS. 3 and 4, a smooth edge dual action tongue scraper 40 is shown. The tongue scraper 40 includes opposed first and second generally planar end portions 42 and 44, respectively, with each end portion terminating distally in a generally elliptical arcuate edge 46 and 48, respectively, and each having therethrough a hole 42H and 44H, respectively. Each end portion 42 and 44 extends proximally in a neck 50 and 52, respectively, with each neck having first and second arcuate edges 50A, 50B, 52A, and 52B, respectively, tapering to a predetermined width. The edges 50A, 52A, 50B and 52B each have a smooth surface. The tongue scraper 40 further includes a generally planar central portion 60 disposed symmetrically between and smoothly contiguous to the end portion necks 50 and 52. The central portion 60 is defined longitudinally by a convexly arcuate first edge 62 having a smooth surface, and a generally linear second edge 64 having a smooth surface.

The tongue scrapers 10 and 40 are fabricated from a resilient material so that if the central portion 30 or 60 is bent into an arc, the scraper immediately will return to its normally planar state once the end portions are released. Preferably, tongue scrapers 10 and 40 are fabricated by the injection molding of polypropylene, as discussed in detail below.

According to each of the preferred embodiments of the present invention, the tongue scraper has a length, Dimension F, of approximately 7.625 inches; a width, Dimension I, at each end portion 42 and 44 of approximately 1 inch; a width, Dimension G, at the central portion 60 of approximately 0.5 inch; and a width, Dimension H, where the central portion 60 attaches to each end portion 42 and 44 of approximately 0.375 inch. However, these dimensions are by way of example only and not by way of limitation. Those skilled in the art will appreciate that various other dimensions are likewise suitable.

Referring now to FIGS. 5–14, the tongue scraper of the present invention is configured so as to provide either a hard scrape or a soft scrape, as desired. A hard scrape is generally more effective in the removal of the undesirable coating on the tongue. However, a soft scrape may be desirable when a soft scrape is sufficient to adequately remove the coating or when the hard scrape is deemed to be too harsh.

A hard scrape is typically effected by bending the tongue scraper in a first direction and a soft scrape is typically effected by bending the tongue scraper in a second, opposite direction, as discussed in detail below.

With particular reference to FIGS. 5 and 6, the dual action tongue scraper 40 for providing a hard scrape and a soft scrape comprises a strip of flexible material defining a central portion 60 and two handles 114 and 116 formed at the two ends of the central portion 60. The first handle 114 preferably has a hole 42H formed therein and the second handled 116 preferably similarly has a hole 44H formed therein, such that the holes 42H and 44H aid in grasping the handles 114 and 116 during use, as discussed above.

The tongue scraper 40 further comprises a first edge 62 and a second edge 64. The first 62 and second 64 edges may be either smooth (as shown in FIGS. 3 and 4) or serrated (as shown in FIGS. 1 and 2), as desired. The first 62 and second 64 edges may also be either substantially straight or convex, as desired.

With particular reference to FIG. 7, the first edge 62 comprises a hard scraping surface defined by orthogonal corner 126A for effecting a hard scrape and a soft scraping surface defined by obtuse corner 128A for effecting a soft scrape. The second edge 64 (FIG. 6) preferably similarly comprises a hard scraping surface and a soft scraping surface.

Each edge 62 and 64 further comprises a generally flat portion 125 (which is generally flat in cross section as shown in FIGS. 6–11, but which may optionally curve when viewed from the side, as when the edge is serrated as shown in FIGS. 10 and 11). The generally flat portion separates the orthogonal corner 126A from the obtuse corner 128A by a distance, Dimension A of FIG. 7, which is sufficient to permit scraping of the tongue with only a desired one of the hard scraping surface defined by the orthogonal corner 126A and the soft scraping surface defined by the obtuse corner 128A. The generally flat portion 125 preferably separates the hard orthogonal corner 126A from the obtuse corner 128A by a distance, Dimension A, of between approximately 0.010 inch and approximately 0.040 inch, preferably approximately 0.020 inch. This separation of the hard scraping surface from the soft scraping surface by the generally flat portion 125 of each edge 62 and 64 thus tends to prevent undesirable contact of both the hard scraping surface and the soft scraping surface with the tongue simultaneously (as will be better appreciated from an examination of FIGS. 13 and 14, which are discussed in detail below). Thus, the separation of the orthogonal corner 126A from the obtuse corner 128A allows the user to more easily use the desired one of the hard scraping surface and the soft scraping surface to scrape the tongue.

Each hard scraping surface, as defined by orthogonal corner 126A, is formed along a substantial portion of the flexible strip, e.g., along at least the central portion 60 thereof, such that the hard scraping surface extends generally from the first handle 114 to the second handle 116. Each soft scraping surface, as defined by obtuse corner 128A, is similarly formed along a substantial portion of the flexible strip, e.g., along at least the central portion 60 thereof, such that the soft scraping surface also extends generally from the first handle 114 to the second handle 116.

It is important to note that either the first edge 62, the second edge 64, or both the first 62 and second 64 edges, may comprise a hard scraping surface and/or a soft scraping surface, as desired. Thus, a hard scraping surface extends along at least one of the first 62 and second 64 edges and a soft scraping surface similarly extends along at least one of the first 62 and second 64 edges, such that the tongue scraper 40 comprises both a hard scraping surface and a soft scraping surface and is thus capable of providing both a hard scrape and a soft scrape.

The hard scraping surface preferably comprises a generally orthogonal corner 126A defining an angle of approximately 90 degrees and the soft scraping surface preferably comprises an obtuse corner 128A defining an angle, Angle B (FIG. 7), of approximately 108 degrees.

According to each of the preferred embodiments of the present invention, the tongue scraper has a thickness, Dimension J, of approximately 0.03 inch. However, those skilled in the art will appreciate that other thicknesses may likewise be suitable, particularly when different materials are utilized. It has been found that the thickness of 0.03 inch provides a desired amount of stiffness when the tongue scraper is manufactured of polypropylene. Thus, it is anticipated that various other combinations of materials and thicknesses may similarly be utilized to provide a desired degree of stiffness.

With particular reference to FIGS. 8 and 9, the soft scraping surface optionally comprises a round corner 128B. As those skilled in the art will appreciate, such a round corner 128B provides softer scraping than the obtuse corner 128A of FIGS. 6 and 7.

With particular reference to FIGS. 10 and 11, the first edge 62(as well as the second edge 64, if desired) of the dual action tongue scraper 10 (better shown in FIGS. 1 and 2) optionally comprises serrations 34. Further, either the first edge 62 or the second edge 64 may be configured so as to be either generally straight or convex, as discussed above.

With particular reference to FIG. 12, an even harder scrape may be obtained by defining the hard scraping surface as a protrusion 126B which extends, Dimension C, between approximately 0.004 inch and approximately 0.012 inch, preferably approximately 0.008 inch, beyond the edge 62 of the tongue scraper 40. The protrusion 126B preferably has an average thickness, Dimension D, of between approximately 0.0005 inch and approximately 0.005 inch, preferably approximately 0.001 inch.

As those skilled in the art will appreciate, the protrusion 126B provides an even more effective, although even more harsh, scrapping action than the orthogonal corner 126A defining the hard scraping surface of FIG. 7. Thus, the protrusion 126B may be utilized to remove difficult tongue coatings, if desired.

With particular reference to FIGS. 13 and 14, orientation of the tongue scraper 40 with respect to a tongue 132 is shown for both a soft scrape (FIG. 13) and a hard scrape (FIG. 14). As can be seen, when the round corner 128B is used to effect a soft scrape, as shown in FIG. 13, then the protrusion 126B does not substantially contact the tongue 132. A soft scrape may similarly be effected by using the obtuse corner 128A of FIG. 7. When the protrusion 126B is used to effect a hard scrape as shown in FIG. 14, then the round corner 128B does not substantially contact the tongue 132. A hard scrape may similarly be effected by using the orthogonal corner 126A of FIG. 7.

The generally flat portion 125 of the edge 62, 64 separates the hard scraping surface from the soft scraping surface by a distance (Dimension A in FIG. 7) which is sufficient to generally cause only one of the hard corner 126B and the soft corner 128B to contact the tongue 132 at any given time during scraping.

Any desired combination of orthogonal corner, obtuse corner, round corner, or protrusion may be formed upon the first 62 and second 64 edges of the tongue scraper 10 or 40 of the present invention, as desired. Thus, a generally more effective tongue scraper may be defined by forming an orthogonal corner and a protrusion on each of the two edges of the tongue scraper, while a generally milder tongue scraper may be defined by forming an obtuse corner and a round corner on each of the two edges thereof, for example.

Alternatively, all four types of corners, i.e., round, obtuse, orthogonal and protrusion, may be embodied in a single tongue scraper by, for example, forming a round corner and an obtuse corner on one edge of the tongue scraper and forming an orthogonal corner and a protrusion on the other edge thereof. Thus, any desired combination of the round corner, obtuse corner, orthogonal corner and protrusion may be provided.

Having described the structure of the dual action tongue scraper for providing a hard scrape and/or a soft scrape, it may be beneficial to describe in further detail the use thereof. As shown in FIG. 5, the tongue scraper 40 is typically bent into a generally U-shaped configuration by grasping one handle 114 or 116 in each hand. The tongue scraper 40 is bent such that the desired scraping surface of the desired edge 62 or 64, will be used to effect scraping.

When the dual action tongue scraper 40 is bent such that the soft scraping surface is disposed along the inside of the U-shape, then only the soft scraping surface will substantially contact the tongue 132, so as to effect desired soft scraping thereof as shown in FIG. 13.

Similarly, when the dual action tongue scraper 40 is bent such that the hard scraping surface is disposed along the inside of the U-shape, then only the hard scraping surface will substantially contact the tongue 132, so as to effect desired hard scraping thereof as shown in FIG. 14.

Thus, the user determines whether a hard scrape or a soft scrape is to be effected by the direction in which the tongue scraper 10 or 40 is bent. After bending the tongue scraper 10 or 40 in the desired direction, then the tongue scraper 10 or 40 is used to effect tongue scraping by angling the tongue scraper 10 or 40 downwardly and pulling the tongue scraper 10 or 40 across the upper surface of the tongue 132, generally from back to front. The tongue scraper 10 or 40 is generally angled such that only one corner of one edge thereof contacts the tongue 132 at a time, as shown in FIGS. 13 and 14. In this manner, the user can control which scraping surface of the tongue scraper 10 or 40 is being used to effect scraping, so as to provide either a soft scrape or a hard scrape, as desired.

Alternatively, the desired one of the hard scraping surface and the soft scraping surface may be used to scrape the tongue while keeping the central portion 30 or 60 of the tongue scraper 10 or 40 generally planar, i.e., without substantially bending the tongue scraper 10 or 40.

Referring now to FIGS. 15 and 16, two alternative methods for injection molding tongue scrapers according to the present invention are shown. In each instance, polypropylene having a melt index of approximately 34 grams/10 minutes (as determined per ASTM D1238) is injected into the mold at a temperature of approximately 400° F. and a pressure of approximately 15,000 psi. Other polypropylene materials may also be used, as well as polyethylene, impact polystyrene, ABS or the like.

With particular reference to FIG. 15, an injection mold comprises upper mold section 202A and lower mold section 204A which, taken together, define mold cavity 206A. The mold cavity 206A comprises cavity protrusions 208, which define the protrusions 126B of the molded tongue scraper 40, as shown in FIGS. 12–14.

With particular reference to FIG. 16, the protrusions 126B are alternatively formed by providing a very small gap 210 having a width, Dimension E (not shown to scale, but rather shown in exaggerated proportion for clarity), which results from forming the mating surfaces of the mold sections 202B and 204B to have a flatness of approximately 0.001 inch (wherein the difference between low spots and high spots on the mating surfaces of the mold sections 202B and 204B is approximately 0.001 inch). That is, the width, Dimension E, of the gap 210 is determined by the surface finish (or rather the unevenness) of the two mating surfaces of the mold sections 202B and 204B. Coarser surface finishes (corresponding to rougher mating surfaces) inherently cause a larger width, Dimension E, of the gap 210. Polymer is injected into the cavity 206B at sufficient pressure, approximately 15,000 psi for example, to create a desired degree of flashing to form within gap 210 which defines protrusion 126B.

Various combinations of gap, Dimension E, and polymer injection pressure may be utilized. Generally, the smaller the gap, the higher the polymer injection pressure that will be needed to form a protrusion of a given length, Dimension C. The gap width, Dimension E, determines the average width, Dimension D, of the protrusion.

More particularly, the length, Dimension C, of the protrusion may be varied by varying the gap width, Dimension E, of the mold sections 202B and 204B and/or by varying the polymer injection molding pressure, while the protrusion's average width, Dimension D, may be varied by varying the gap width, Dimension E. However, varying the polymer injection pressure may have some effect upon the average protrusion width, Dimension D, since higher polymer injection pressures may, on some injection molding systems, tend to increase the gap width, Dimension E.

It is understood that the exemplary dual action tongue scrapers described herein and shown in the drawings represent only presently preferred embodiments of the invention. Indeed, various modifications and additions may be made to such embodiments without departing from the spirit and scope of the invention. For example, the tongue scrapers need not be substantially flat or planar in configuration. Rather, the tongue scrapers may be formed so as to have greater thickness near the longitudinal centerline thereof, if desired. Further, various different configurations of the handles are contemplated. For example, T-shaped handles may alternatively be utilized. Thus, these and other modifications and additions may be obvious to those skilled in the art and may be implemented to adapt the present invention for use in a variety of different applications.

The above descriptions of exemplary embodiments of a dual action tongue scraper are for illustrative purposes. Because of variations which will be apparent to those skilled in the art, the present invention is not intended to be limited to the particular embodiments described above. Such variations, and other modifications and alternations, are included within the scope and intent of the invention as described in the following claims.

What is claimed is:

1. A method for scraping a tongue, the method comprising the steps of:

grasping a flexible strip with one hand at each of two ends thereof, the flexible strip having first and second edges and having a hard scraping surface extending at least partially along the first and second edges and having a soft scraping surface extending at least partially along the first and second edges, the hard scraping surface being separated from the soft scraping surface by a generally flat portion of the edge, the generally flat portion of the edge separating the hard scraping surface from the soft scraping surface by a distance which is sufficient to permit scraping of the tongue generally with only a desired one of the hard scraping surface and the soft scraping surface;

bending the flexible strip into a generally U-shaped configuration such that a desired one of the hard scraping surface and the soft scraping surface is along an inside portion of the U-shaped flexible strip; and scraping the tongue with the inside portion of the U-shaped flexible strip.

2. The method for scraping the tongue as recited in claim 1, wherein the step of grasping the flexible strip comprises grasping the flexible strip by handles formed at the two ends thereof.

3. The method for scraping the tongue as recited in claim 1, wherein the step of scraping the tongue with the inside portion of the U-shaped strip comprises scraping the tongue with a straight edge of the flexible strip.

4. The method for scraping the tongue as recited in claim 1, wherein the step of scraping the tongue with the inside portion of the U-shaped strip comprises scraping the tongue with a convex edge of the flexible strip.

5. The method for scraping the tongue as recited in claim 1, wherein the step of scraping the tongue with the inside portion of the U-shaped strip comprises scraping the tongue with a smooth edge of the flexible strip.

6. The method for scraping the tongue as recited in claim 1, wherein the step of scraping the tongue with the inside portion of the U-shaped strip comprises scraping the tongue with a serrated edge of the flexible strip.

7. The method for scraping the tongue as recited in claim 1, wherein the step of scraping the tongue with the inside portion of the U-shaped strip comprises scraping the tongue with a hard scraping surface of the flexible strip.

8. The method for scraping the tongue as recited in claim 1, wherein the step of scraping the tongue with the inside portion of the U-shaped strip comprises scraping the tongue with a soft scraping surface of the flexible strip.

9. The method for scraping the tongue as recited in claim 7, wherein the step of scraping the tongue with a hard scraping surface of the flexible strip comprises scraping the tongue with a generally orthogonal corner of the flexible strip.

10. The method for scraping the tongue as recited in claim 7, wherein the step of scraping the tongue with a hard scraping surface of the flexible strip comprises scraping the tongue with a protrusion formed upon one of the first and second edges.

11. The method for scraping the tongue as recited in claim 8, wherein the step of scraping the tongue with a soft scraping surface of the flexible strip comprises scraping the tongue with an obtuse corner of the flexible strip.

12. The method for scraping the tongue as recited in claim 8, wherein the step of scraping the tongue with a soft scraping surface of the flexible strip comprises scraping the tongue with a round corner of the flexible strip.

13. The method for scraping the tongue as recited in claim 1, wherein the generally flat portion of the edge separates the hard scraping surface from the soft scraping surface by a distance which is between approximately 0.010 inch and approximately 0.040 inch.

14. The method for scraping the tongue as recited in claim 1, wherein the generally flat portion of the edge separates the hard scraping surface from the soft scraping surface by a distance of approximately 0.020 inch.

15. A method for scraping a tongue, the method comprising the steps of:

grasping a strip with one hand at each of two ends thereof, the strip having first and second edges and having a hard scraping surface extending at least partially along the first and second edges and having a soft scraping surface extending at least partially along the first and second edges, the hard scraping surface being separated from the soft scraping surface by a generally flat portion of the edge, the generally flat portion of the edge separating the hard scraping surface from the soft scraping surface by a distance which is sufficient to permit scraping of the tongue generally with only a desired one of the hard scraping surface and the soft scraping surface; and scraping the tongue with a desired one of the hard scraping surface and the soft scraping surface.

16. The method of claim 15, wherein the step of grasping the strip at each of two ends comprises grasping said strip with two circular handles.

17. The method of claim 15 further including the steps of bending said strip in a second orientation such that the other hard or soft scraping surface is now the active scraping surface, and scraping with said active scraping surface.

18. The method of claim 15, wherein the scraper includes a generally flat first and second wall and is configured to easily bend.

19. A method for using a dual-action tongue scraper, said method comprising the steps of:

viewing said tongue scraper and determining which of a hard surface or soft surface on which of a first scraping edge or a second scraping edge to use;

bending said scraper into a U-shaped orientation so that said selected first or second scraping edge and said corresponding hard or soft scraping surface is along an inside radius of said U-shaped orientation;

grasping said bent scraper by its two ends;

scraping a tongue with said hard or soft scraping surface and said first or second scraping edge; and wherein said scraper comprises a generally flat first and second wall and wherein said first and second flat walls extend approximately from one scraping edge to the other, said scraper is further configured to easily bend.

* * * * *